United States Patent
Capracotta et al.

(10) Patent No.: US 9,173,392 B2
(45) Date of Patent: Nov. 3, 2015

(54) EMULSIFIABLE CONCENTRATE

(75) Inventors: Michael D. Capracotta, Canton, MI (US); Laura L. Brasher, Clinton, NJ (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/582,901

(22) PCT Filed: Mar. 4, 2011

(86) PCT No.: PCT/US2011/027151
§ 371 (c)(1),
(2), (4) Date: Oct. 4, 2012

(87) PCT Pub. No.: WO2011/109689
PCT Pub. Date: Sep. 9, 2011

(65) Prior Publication Data
US 2013/0017954 A1 Jan. 17, 2013

Related U.S. Application Data

(60) Provisional application No. 61/311,013, filed on Mar. 5, 2010.

(51) Int. Cl.
*A01N 25/02* (2006.01)
*A01N 25/04* (2006.01)
*A01N 25/22* (2006.01)
*A01N 3/00* (2006.01)
*A01N 25/00* (2006.01)

(52) U.S. Cl.
CPC ............ *A01N 25/02* (2013.01); *A01N 25/04* (2013.01); *A01N 3/00* (2013.01); *A01N 25/00* (2013.01); *A01N 25/22* (2013.01)

(58) Field of Classification Search
CPC ......... A01N 3/00; A01N 25/00; A01N 25/02; A01N 25/04; A01N 25/22
See application file for complete search history.

(56) References Cited

U.S. PATENT DOCUMENTS

| 4,963,574 | A | * | 10/1990 | Bachmann et al. | 514/357 |
| 5,045,109 | A | * | 9/1991 | Nakamura et al. | 504/305 |
| 5,270,286 | A | * | 12/1993 | Ong | 504/130 |
| 6,683,030 | B2 | * | 1/2004 | Kober et al. | 504/313 |
| 2003/0069135 | A1 | | 4/2003 | Kober et al. | |
| 2008/0039646 | A1 | | 2/2008 | Storzum et al. | |

FOREIGN PATENT DOCUMENTS

| CN | 1422115 A | 6/2003 |
| WO | WO 0167860 A1 | 9/2001 |
| WO | WO 2005123821 A2 | 12/2005 |

OTHER PUBLICATIONS

English language abstract for WO 0167860 extracted from espacenet.com database on Jan. 3, 2013, 40 pages.
English language abstract for WO 2005123821 extracted from espacenet.com database on Jan. 3, 2013, 31 pages.
BASF, Hexamoll Dinch 1,2-Cyclohexane Dicarboxylic Acid, Diisononyl Ester, Technical Data Sheet,Apr. 2009, pp. 1-2.
International Search Report for Application No. PCT/US2011/027151 dated Jan. 16, 2012, 4 pages.
English language abstract not found for CN 1422115. However see English language equivalent U.S. 2003/0069135. Original document extracted from espacenet.com database Apr. 17, 2014, 31 pages.

* cited by examiner

*Primary Examiner* — Ali Soroush
(74) *Attorney, Agent, or Firm* — Howard & Howard Attorneys PLLC

(57) ABSTRACT

An emulsifiable concentrate (EC) is provided. The EC includes an active component, a solvent component, and an emulsifier component. The active component is present in an amount of from 20 to 90 parts by weight per 100 parts by weight of the emulsifiable concentrate. The solvent component includes 1,2-cyclohexanedicarboxylic acid diisononyl ester. The emulsifier component is present in an amount of from 5 to 15 parts by weight per 100 parts by weight of the emulsifiable concentrate and includes an anionic surfactant, a non-ionic surfactant, and a surfactant including at least one ethylene oxide block. Moreover, the active component is dissolved in the solvent component.

25 Claims, No Drawings

EMULSIFIABLE CONCENTRATE

RELATED APPLICATIONS

This application is the National Stage of International Patent Application No. PCT/US2011/027151, filed on Mar. 4, 2011, which claims priority to and all the advantages of U.S. Provisional Patent Application No. 61/311,013, filed on Mar. 5, 2010.

FIELD OF THE INVENTION

The subject invention generally relates to an emulsifiable concentrate. More specifically, the emulsifiable concentrate includes an active component, a solvent component, and an emulsifier component. The active component is dissolved in the solvent component.

DESCRIPTION OF THE RELATED ART

There is an increasing demand for better performing and environmentally acceptable crop protection products in the market. This demand is a driving force for continuous innovation and has focused efforts on development of crop protection products that are easy to handle and have high levels of activity.

As is well known in the art, there different types of crop protection products that include active ingredients (e.g. pesticides). Emulsions in water ("EW") typically include a non-polar dispersed phase in an aqueous continuous phase. Wettable powders ("WP") include solid active ingredients that cannot be easily diluted in common solvents and, as such, are sold as wettable powders which form stable dispersions when mixed with water. Suspension concentrates ("SC") include solid active ingredients dispersed in liquids. Suspoemulsions typically include oil phases as emulsions in water and solid phases dispersed in the water. Soluble liquids typically include liquid active ingredients that are miscible in water or other solvents.

An additional type of crop protection product is an emulsifiable concentrate (EC) Typically, ECs include solid or liquid active ingredients dissolved in organic solvents. The most common organic solvents are aromatic solvents such as Aromatic 200. However, attempts have been made to replace typical aromatic solvents to dissolve active ingredients in solution. However, such attempts usually require large loadings of expensive surfactants and large volumes of solvents as compared to amounts of active ingredients. Accordingly, there remains an opportunity to develop an emulsifiable concentrate that has a low VOC content, that does not require large loadings of expensive surfactants, and that can dissolve desired amounts of active ingredients in solution.

SUMMARY OF THE INVENTION AND ADVANTAGES

The instant invention provides an emulsifiable concentrate that includes an active component, a solvent component, and an emulsifier component. The active component is present in an amount of from 20 to 90 parts by weight per 100 parts by weight of the emulsifiable concentrate. The solvent component includes 1,2-cyclohexanedicarboxylic acid diisononyl ester. The emulsifier component is present in an amount of from 5 to 15 parts by weight per 100 parts by weight of the emulsifiable concentrate and includes an anionic surfactant, a non-ionic surfactant, and a surfactant different from the anionic surfactant and the non-ionic surfactant and including at least one ethylene oxide block. Moreover, the active component is dissolved in the solvent component.

The 1,2-cyclohexanedicarboxylic acid diisononyl ester (commonly known in the art as Hexamoll® Dinch) is a low VOC and low odor solvent that effectively dissolves a wide variety of active components. In addition, the Hexamoll® Dinch has an excellent toxicological profile and is inexpensive to use. The emulsifier component contributes to superior bloom and storage stability of the emulsifiable concentrate. In other words, the emulsifier component allows the active component to effectively mix with, and remain dissolved in, the solvent component. The particular amount of the emulsifier component that is used in this invention minimizes production costs while maintaining the stability and commercial usefulness of the emulsifiable concentrate.

DETAILED DESCRIPTION OF THE INVENTION

The present invention provides an emulsifiable concentrate (also known in the art as an "EC"). The emulsifiable concentrate is typically a liquid that has a viscosity of from 1 to 200, 50 to 200, 100 to 200, or less than or equal to about 200, cps at 25° C. Without intending to be bound by any particular theory, it is believed that a viscosity of less than or equal to about 200 cps at 25° C. promotes blooming and efficient formation of an emulsion when the emulsifiable concentrate is used. In one embodiment, the emulsifiable concentrate is further defined as a crop protector or a crop protection formulation.

The emulsifiable concentrate is typically anhydrous, i.e., free of water. However, the emulsifiable concentrate may include less than 5, less than 2.5, less than 1, less than 0.5, or less than 0.1, parts by weight of water per 100 parts by weight of the emulsifiable concentrate. Most typically, the emulsifiable concentrate is a single oil-like, e.g. hydrophobic, phase that does not include water. If added to water or another solvent, the emulsifiable concentrate preferably forms a milky white agricultural emulsion that blooms and that has little to no phase separation, as is described in greater detail below.

The emulsifiable concentrate includes an active component, a solvent component, and an emulsifier component. The active component is commonly known in the art as an "active ingredient." In one non-limiting embodiment, the active component is further defined as a pesticide. In another embodiment, the active component is as defined in U.S. Pat. No. 6,683,030, which is expressly incorporated herein by reference relative to the active component. Suitable but not limiting examples of active components include Propanil, Endosulfan, Metolachlor, Malathion, and the like.

The terminology "pesticide," as used herein, is well known in the art and is described at least by the Environmental Protection Agency (EPA), in the Federal Insecticide, Fungicide, and Rodenticide Act (FIFRA), in the Insecticides and Environmental Pesticide Control Subchapter (7 U.S.C. §136 (u)), in the Code of Federal Regulations (CFR) relating to the "Protection of Environment," and in the Regulations of the EPA in 40 CFR §152.3. A pesticide is typically recognized in the art as a substance that is used for preventing, destroying, repelling, regulating, and/or mitigating any pest. A pest is an organism that is deleterious to man or the environment but does not include any internal parasite of living man or other living animal or any fungus, bacterium, virus, or other microorganism on or in living man or other living animals. Said differently, the terminology "pest" does not typically include any organism that infects or sickens humans or animals. In addition, the terminology "pesticide," as used herein, does not typically include any human or animal drugs or pharmaceuticals, any article that is a "new animal drug" as defined in the art, any liquid sterilant applied to a device used in the human body, and/or any products intended for use against fungi, bacteria, viruses, or other microorganisms in or on living man or living animal. Moreover, the pesticide of this invention does not typically include drugs or pharmaceuticals used to control diseases of humans or animals (such as livestock and pets).

In various embodiments, the active component includes, consists essentially of, or consists of, one or more herbicides, such as agricultural herbicides that can be applied to plants and or leaves of plants, fungicides, insecticides, and the like. Typically, if the active component consists essentially of the herbicides, fungicides, and/or insecticides, the active component is free of compounds that materially affect the basic and novel characteristics of the active component such as those compounds which are not pesticides.

The active component may also include additional chemical compounds that are not pesticides or active ingredients. Examples include, but are not limited to, activators, antifeedants, anti-fouling agents, attractant agents, chemosterilants, disinfectant agents, fumigant agents, pheromones, repellent agents, defoliants, desiccants, insect growth regulators, plant growth regulators, synergists, adjuvants, and combinations thereof.

The active component is present in an amount of from 20 to 90 parts by weight per 100 parts by weight of the emulsifiable concentrate. In various embodiments, the active component is present in amounts of from 20 to 30, 20 to 40, 30 to 40, 40 to 50, 50 to 60, 60 to 70, 70 to 80, 80 to 90, 25 to 35, 35 to 45, 45 to 55, 55 to 65, 65 to 75, 75 to 85, or 20 to 60, 30 to 60, 60 to 90, 40 to 60, 60 to 90, or 20 to 60, parts by weight per 100 parts by weight of the emulsifiable concentrate. In other embodiments, the active component is present in amounts of from 20 to less than 60, from 30 to less than 60, from 40 to less than 60, from 50 to less than 60, from 60 to less than 90, from 60 to less than 80, or from 60 to less than 70, parts by weight per 100 parts by weight of the emulsifiable concentrate. Of course, it is to be understood that the instant invention is not limited to the aforementioned values and that the active component may be present in any whole or fractional amount or range of amounts within the aforementioned values. The active component is typically dissolved in the solvent component in the formation of the overall emulsifiable concentrate.

Referring back to the solvent component, the solvent component includes 1,2-cyclohexanedicarboxylic acid diisononyl ester, which is commonly known in the art, and referred to hereinafter, as Hexamoll® Dinch (CAS-Number 166412-78-8), which is commercially available from BASF Corporation. In various embodiments, the solvent component includes a mix of isomers of 1,2-cyclohexanedicarboxylic acid diisononyl ester, e.g. a mix of branched and linear isomers. It is contemplated that the solvent component may include only the branched isomer or only the linear isomer or a mixture of isomers. For descriptive purposes only, a chemical structure of 1,2-cyclohexanedicarboxylic acid diisononyl ester is set forth below:

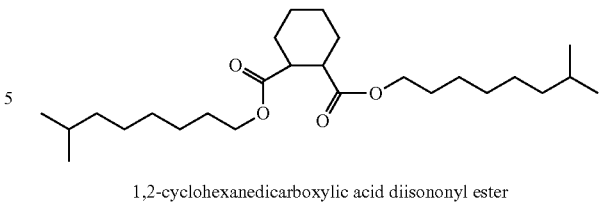

1,2-cyclohexanedicarboxylic acid diisononyl ester

The solvent component may also include a second solvent, such as a co-solvent. Suitable, but non-limiting, co-solvents include cyclohexanone, polyethylene glycol, propylene carbonate, propylene glycol, and combinations thereof. In various embodiments, the solvent component includes from 70 to 85 weight percent of Hexamoll® Dinch and from 15 to 30 weight percent of a co-solvent. In various other embodiments, the EC includes from 30 to 40 weight percent of Hexamoll® Dinch and 1 to 20 weight percent of a co-solvent. The amount of co-solvent can be customized to dissolve the active component and/or improve solubility of the emulsifier component.

The Hexamoll® Dinch may be present in any amount in the solvent component. In various embodiments, the Hexamoll® Dinch and/or the co-solvent may be present in the solvent component in amounts of from 0.1 to 99, from 1 to 95, from 10 to 90, from 1 to 10, from 10 to 20, from 20 to 30, from 30 to 40, from 40 to 50, from 50 to 60, from 60 to 70, from 5 to 15, from 15 to 25, from 25 to 35, from 35 to 45, from 45 to 55, from 55 to 65, or from 65 to 75, parts by weight per 100 parts by weight of the solvent component. In other embodiments, the Hexamoll® Dinch and/or the co-solvent may be present in amounts of less than 95, less than 85, less than 80, less than 75, less than 70, less than 65, less than 60, less than 55, less than 50, less than 45, less than 40, less than 35, less than 30, less than 25, less than 20, less than 15, less than 10, less than 5, or less than 1, part by weight per 100 parts by weight of the solvent component. In one embodiment, the solvent component includes 100 percent by weight of the Hexamoll® Dinch. Of course, it is to be understood that the instant invention is not limited to the aforementioned values and that the Hexamoll® Dinch and/or the co-solvent may be present in any whole or fractional amount or range of amounts within the aforementioned values.

The solvent component may consist essentially of the Hexamoll® Dinch or consist of the Hexamoll® Dinch. The terminology "consist essentially of" refers to the solvent component being free from solvents that materially affect the basic and novel characteristics of the solvent component, such as Aromatic 200. Alternatively, the solvent component may consist essentially of the Hexamoll® Dinch and the co-solvent, pursuant to the description above. In another embodiment, the solvent component consists of the Hexamoll® Dinch and the co-solvent.

The solvent component is typically present in the emulsifiable concentrate in an amount such that a total amount of the active component, the solvent component, and the emulsifier component is approximately equal to 100 weight percent of the emulsifiable concentrate. In other words, the solvent component is typically present as a "balance" to the active component and the emulsifier component. In various embodiments, the solvent component is present in amounts of from 0.1 to 75, from 0.1 to 10, from 1 to 10, from 10 to 20, from 20 to 30, from 30 to 40, from 40 to 50, from 50 to 60, from 60 to 70, from 5 to 15, from 15 to 25, from 25 to 35, from 35 to 45, from 45 to 55, from 55 to 65, or from 65 to 75, parts by weight per 100 parts by weight of the emulsifiable concentrate. In other embodiments, the solvent component is present in amounts of less than 75, less than 70, less than 65, less than 60, less than 55, less than 50, less than 45, less than 40, less than 35, less than 30, less than 25, less than 20, less than 15, less than 10, less than 5, or less than 1, part by weight per 100 parts by weight of the emulsifiable concentrate. Of course, it is to be understood that the instant invention is not limited to the aforementioned values and that the solvent component may be present in any whole or fractional amount or range of amounts within the aforementioned values.

In addition to the solvent component, the emulsifiable concentrate also includes the emulsifier component. The emulsifier component is present in an amount of from 5 to 15 parts by weight, and may alternatively be present in amount of from 5 to 10 or 10 to 15, parts by weight, per 100 parts by weight of the emulsifiable concentrate. The emulsifier component includes three types of surfactants: an anionic surfactant, a non-ionic surfactant, and a surfactant that is different from the anionic surfactant and the non-ionic surfactant and that includes at least one ethylene oxide block. Without intending to be bound by any particular theory, it is believed that if the emulsifier component is included in an amount less than 5 parts by weight or in an amount of greater than 15 parts by weight, a successful emulsion may not form when the emulsifiable concentrate is added to water or another solvent at point of use, as first described above. The emulsifiable concentrate is also typically dissolved in the solvent component.

The anionic surfactant may be any known in the art and typically includes alkali, alkaline earth or ammonium salts of fatty acids, such as potassium stearate, alkyl sulfates, alkyl ether sulfates, alkylsulfonates or iso-alkylsulfonates, alkylbenzenesulfonates such as sodium dodecylbenzenelsulfonate and calcium dodecylbenzene sulfonate, alkylnaphthalenesulfonates, alkyl methyl ester sulfonates, acyl glutamates, alkylsulfosuccinates, sarcosinates such as sodium lauroyl sarcosinate or taurates, and combinations thereof. In various embodiments, the anionic surfactant is further defined as calcium dodecylbenzene sulfonate or calcium dodecylbenzene sulfonate in 2-ethylhexanol. It is also contemplated that the anionic surfactant may be further defined as one or mixture of surfactants that are commercially available from AkzoNobel under the trade name of Witconate®.

The anionic surfactant may be present in the emulsifier component in any amount. In various embodiments, the anionic surfactant is present in amounts of from 10 to 90, from 20 to 80, from 30 to 60, from 40 to 50, from 40 to 60, from 50 to 60, from 40 to 70, or from 30 to 80, parts by weight per 100 parts by weight of the emulsifier component. In another embodiment, the anionic surfactant is present in a weight ratio to the non-ionic surfactant and to the surfactant (that is different from the anionic surfactant and the non-ionic surfactant) including at least one ethylene oxide block of 2:1:1. Of course, it is to be understood that the instant invention is not limited to the aforementioned values and that the anionic surfactant may be present in any whole or fractional amount or range of amounts within the aforementioned values.

The non-ionic surfactant may be any known in the art and typically includes alkoxylated animal or vegetable fats and oils such as corn oil ethoxylates, castor oil ethoxylates, talo fat ethoxylates, glycerol esters such as glycerol monostearate, fatty alcohol alkoxylates and oxoalcohol alkoxylates, fatty acid alkoxylates such as oleic acid ethoxylates, alkylphenol alkoxylates such as isononylphenol ethoxylates, fatty amine alkoxylates, fatty acid amide alkoxylates, sugar surfactants such as sorbitan fatty acid esters (e.g. sorbitan monooleate, and sorbitan tristearate), polyoxyethylene sorbitan fatty acid esters, alkyl polyglycosides, N-alkylgluconamides, alkylmethyl sulfoxides, alkyldimethylphosphine oxides such as tetradecyldimethylphosphine oxide, and combinations thereof. In various embodiments, the non-ionic surfactant is further defined as a castor oil ethoxylate wherein the castor oil is ethoxylated with 40 to 54 or 40 to 50, moles of ethylene oxide. It is also contemplated that the non-ionic surfactant may be further defined as one or a mixture of surfactants that are commercially available from AkzoNobel under the trade name of Emulpon® and/or from BASF Corporation under the trade name of Cremophor®. In one embodiment, the non-ionic surfactant is further defined as a combination of two individual surfactants wherein one surfactant is ethoxylated with from 40 to 54 moles of ethylene oxide and the second surfactant is ethoxylated with from 4 to 15 moles of ethylene oxide. In other embodiments, the non-ionic surfactant includes propoxylation, i.e., is propoxylated with propylene oxide.

The non-ionic surfactant may be present in the emulsifier component in any amount. In various embodiments, the non-ionic surfactant is present in amounts of from 10 to 90, from 20 to 80, from 30 to 60, from 40 to 50, from 50 to 60, from 40 to 70, from 30 to 80, or from 20 to 30, parts by weight per 100 parts by weight of the emulsifier component. In another embodiment, the non-ionic surfactant is present in a weight ratio to the anionic surfactant and to the surfactant including the at least one ethylene oxide block of 1:2:1. Of course, it is to be understood that the instant invention is not limited to the aforementioned values and that the non-ionic surfactant may be present in any whole or fractional amount or range of amounts within the aforementioned values.

The surfactant that is different from the anionic surfactant and the non-ionic surfactant and that includes the at least one ethylene oxide block may be referred to as an "ethylene oxide block copolymer surfactant." This surfactant may be any known in the art and typically includes di-, tri- or multi-block polymers of the $(AB)_x$ (wherein x is a positive number), ABA and BAB type, AB comb polymers, and combinations thereof. In various embodiments, this surfactant includes an initiator core that is ethoxylated with from 2 to 55 moles of ethylene oxide. Suitable, non-limiting examples of initiator cores include nonylphenol, propylene oxide, castor oil, alcohols such as those having from two to sixteen carbon atoms, and combinations thereof. It is contemplated that the surfactant that includes the at least one ethylene oxide block may include only ethylene oxide blocks and no other alkylene oxide blocks, such as propylene oxide blocks. Alternatively, the surfactant that includes the at least one ethylene oxide block may also include one or more than one propylene oxide block.

In one embodiment, the emulsifier component may also include a surfactant that includes a propylene oxide block, which can also be referred to as a "propylene oxide block copolymer surfactant." This surfactant is also different from the anionic surfactant and the non-ionic surfactant. It is contemplated that the surfactant including the at least one ethylene oxide block and/or the propylene oxide block copolymer surfactant may be further defined as one or a mixture of surfactants commercially available from BASF Corporation under the trade names of Pluriol®, Pluronic®, and Lutensol®, and/or from The Dow Chemical Company under the trade name of Tergitol®.

The surfactant including the at least one ethylene oxide block may be present in the emulsifier component in any amount. In various embodiments, the surfactant including the at least one ethylene oxide block is present in amounts of from 10 to 90, from 20 to 80, from 30 to 60, from 40 to 50, from 50 to 60, from 40 to 70, from 30 to 80, or from 20 to 30, parts by weight per 100 parts by weight of the emulsifier component. In another embodiment, the surfactant including the at least one ethylene oxide block is present in a weight ratio to the anionic surfactant and the non-ionic surfactant of 1:2:1. Of course, it is to be understood that the instant invention is not limited to the aforementioned values and that the surfactant including the at least one ethylene oxide block may be present in any whole or fractional amount or range of amounts within the aforementioned values.

The EC of this invention primarily includes a single phase. In other words, the EC of this invention does not typically include a distinct non-polar phase and a distinct polar phase but instead typically includes a single phase that includes the active component, the solvent component, and the emulsifier component. Of course, it is to be appreciated that the single phase of this invention may include partial phase separation but does typically include total phase separation. Most typically, there is no visually detectable phase separation of the instant EC at temperatures between at least 10° C. and 50° C. However, at low temperatures, phase separation may occur.

As is described in greater detail below, the emulsifiable concentrate may be added to water or another solvent to form an agricultural emulsion at point of sale and/or use. Typically, well formed agricultural emulsions are milky in color, spontaneously bloom (i.e., form), and have less than 1 mm of separation between phases. However, agricultural emulsions of this invention are not limited to such parameters and may have other characteristics that are indicative of successful emulsion formation.

In various embodiments, the active component is present in an amount of about 60 parts by weight per 100 parts by weight of the emulsifiable concentrate. In addition, the anionic surfactant, the nonionic surfactant, and the surfactant including at least one ethylene oxide block may be present in the emulsifier component in a weight ratio of about 2:1:1, respectively. Moreover, the emulsifier component may present in an amount of from about 5 to 7 parts by weight per 100 parts by weight of the emulsifiable concentrate. Still further, the solvent component may consist essentially of 1,2-cyclohexanedicarboxylic acid diisononyl ester and be present in an amount of from about 33 to 35 parts by weight per 100 parts by weight of the emulsifiable concentrate. In this embodiment, the terminology "consist essentially of" typically describes the solvent component being free of amounts of other solvents that would affect the basic and novel characteristics of the 1,2-cyclohexanedicarboxylic acid diisononyl ester. Said differently, the solvent component may consist essentially of the 1,2-cyclohexanedicarboxylic acid diisononyl ester and include amounts of other solvents so long as those other solvents do not affect the ability of the 1,2-cyclohexanedicarboxylic acid diisononyl ester to form successful emulsions and/or affect the VOC content of the solvent component by more than 5, 10, 15, or 20%. In addition, the emulsifiable concentrate may include less than 1 part by weight of water per 100 parts by weight of the emulsifiable concentrate.

EXAMPLES

Determination of VOC Content:

A series of solvents are evaluated to determine a content of volatile organic compounds (VOCs) and suitability for use in this invention. More specifically, the 1,2-cyclohexanedicarboxylic acid diisononyl ester (Hexamoll® Dinch) of this invention is evaluated as Solvent 1. Twelve additional comparative solvents (Comparative Solvents 1-12) are also evaluated.

To evaluate the VOC content, 10 mg aliquots of each of the Solvent 1 and the Comparative Solvents 1-13 are individually placed on DSC disposable aluminum pans which are previously dried at 125° C. for one hour and stored in a desiccator. After addition of the aliquots to the pans, the pans are placed in a furnace at 35° C. The temperature of the furnace is then raised at a rate of 5° C. per minute and held isothermally at 115° C. When mass loss stabilizes at less than 0.5% for 5 minutes, the temperature is then held at 115° C. for an additional 15 minutes. Total run times average about 80 minutes. The results of the VOC content evaluations are set forth in Table 1 below wherein all values represent percentage weight loss of the aliquot and correlate to approximate VOC content.

TABLE 1

| Samples of Solvents | % Total Weight Loss = VOC Content |
|---|---|
| Solvent 1 | 0.33 |
| Comparative Solvent 1 | 100 |
| Comparative Solvent 2 | 100 |
| Comparative Solvent 3 | 21.1 |
| Comparative Solvent 4 | 0.62 |
| Comparative Solvent 5 | 100 |
| Comparative Solvent 6 | 99.9 |
| Comparative Solvent 7 | 100 |
| Comparative Solvent 8 | 100 |
| Comparative Solvent 9 | 100 |
| Comparative Solvent 10 | 100 |
| Comparative Solvent 11 | 100 |
| Comparative Solvent 12 | 1.3 |

The Solvent 1 is the 1,2-cyclohexanedicarboxylic acid diisononyl ester (Hexamoll ® Dinch) of this invention.
The Comparative Solvent 1 is commercially available from BASF Corporation under the trade name of Protectol ® PE.
The Comparative Solvent 2 is commercially available from ExxonMobil under the trade name of Aromatic 200.
The Comparative Solvent 3 is a butyl initiated alcohol alkoxylate that is propoxylated with 3.3 moles of propylene oxide and ethoxylated with 0.9 moles of ethylene oxide.
The Comparative Solvent 4 is 2-propyl heptanol that is ethoxylated with 0.5 moles of ethylene oxide and propoxylated with 10 moles of propylene oxide.
The Comparative Solvent 5 is propylene carbonate.
The Comparative Solvent 6 is commercially available from Purac America, Inc. under the trade name of Purasolv ® EHL.
The Comparative Solvent 7 is propylene glycol.
The Comparative Solvent 8 is commercially available from the Stepan Company under the trade name of Hallcomid ® M-8-10.
The Comparative Solvent 9 is commercially available from The Dow Chemical Company under the trade name of Estasol ®.
The Comparative Solvent 10 is dimethyl adipate.
The Comparative Solvent 11 is commercially available from Cognis under the trade name Agnique ® ME 610-U.
The Comparative Solvent 12 is commercially available from Cognis under the trade name Agnique ® ME-18S-U.

The results set forth in Table 1 above demonstrate that the Solvent 1, i.e., the 1,2-cyclohexanedicarboxylic acid diisononyl ester (Hexamoll® Dinch), of this invention has a lower VOC content than the comparative solvents and thus is particularly suitable for use in the emulsifiable concentrate of this invention.

Determination of Active Component Solubility in Various Solvents at 10° C. and 54° C.:

A series of solvents is also evaluated relative to solubility of three common active components (i.e., pesticides): Metolachlor, Malathion, and Propanil. Relative to Solvent 1, Examples 1-3 are prepared and demonstrate the Metolachlor, Malathion, and Propanil are each miscible in the Solvent 1 up to approximately 66 weight percent.

Example 1 is prepared by adding 20 grams of Metolachlor to 10 grams of Solvent 1.

Example 2 is prepared by adding 20 grams of Malathion to 10 grams of Solvent 1.

Example 3 is prepared by adding 5 grams of Propanil to 10 grams of Solvent 1.

Each of Examples 1-3 is prepared in duplicate. A first sample of Examples 1-3 is placed in a refrigerator at 10° C. A second sample of Examples 1-3 is placed in an oven at 54° C. The samples are maintained at these temperatures for approximately two weeks. After this time, the samples are visually evaluated to determine whether any Metolachlor, Malathion, or Propanil is undissolved.

For any samples that include undissolved active components, the liquid of these samples is removed and vacuumed filtered through #1 filter paper to remove any undissolved solids. Subsequently, the filtered liquid is analyzed to determine a maximum solubility using high performance liquid chromatography (HPLC) using a Water Aquity UPCL system, acetonitrile as a solvent, and an external Propanil standard. The results of these evaluations are set forth in Table 2 below.

Relative to the Comparative Solvents 1-12, each of these solvents is also evaluated to determine at what weight percents Metolachlor, Malathion, and Propanil are miscible therein. Comparative Examples (A1-L1; A2-L2; and A3-L3) are prepared to evaluate Comparative Solvents 1-13 and Metolachlor, Malathion, and Propanil, respectively. These Comparative Examples are detailed below.

Comparative Examples A1-L1 are prepared by adding 20 grams of Metolachlor to 10 grams of each of the Comparative Solvents 1-13. Each of Comparative Examples A1-L1 is prepared in duplicate, as described above. One sample of each of the Comparative Examples A1-L1 is placed in a refrigerator at 10° C. while a second sample of each is placed in an oven at 54° C. The samples are maintained at these temperatures for approximately two weeks. After this time, the samples are evaluated, as described above. The results of these evaluations are set forth in Table 2 below.

Comparative Examples A2-L2 are prepared by adding 20 grams of Malathion to 10 grams of each of the Comparative Solvents 1-13. Each of Comparative Examples A2-L2 is prepared in duplicate, as described above. One sample of each of the Comparative Examples A2-L2 is placed in a refrigerator at 10° C. while a second sample of each is placed in an oven at 54° C. The samples are maintained at these temperatures for approximately two weeks. After this time, the samples are evaluated, as described above. The results of these evaluations are also set forth in Table 2 below.

Comparative Examples A3-L3 are prepared by adding 5 grams of Propanil to 10 grams of each of the Comparative Solvents 1-13. Each of Comparative Examples A3-L3 is prepared in duplicate, as described above. One sample of each of the Comparative Examples A3-L3 is placed in a refrigerator at 10° C. while a second sample of each is placed in an oven at 54° C. The samples are maintained at these temperatures for approximately two weeks. After this time, the samples are evaluated, as described above. The results of these evaluations are also set forth in Table 2 below.

TABLE 2

| Approximate Percent (%) Solubility Determination of Active Components in Solvents | Example 1, Comparative Examples A1-L1 (Metolachlor At 10° C.) | Example 2, Comparative Examples A2-L2 (Malathion At 10° C.) | Example 3, Comparative Examples A3-L3 (Propanil At 10° C.) |
|---|---|---|---|
| Solvent 1 | Totally Soluble | Totally Soluble | 28.4% |
| Comparative Solvent 1 | Totally Soluble | Totally Soluble | 23.9 |
| Comparative Solvent 2 | Totally Soluble | Totally Soluble | 2.89% |
| Comparative Solvent 3 | Totally Soluble | Totally Soluble | 16.0% |
| Comparative Solvent 4 | Totally Soluble | Totally Soluble | 12.5% |
| Comparative Solvent 5 | Totally Soluble | Totally Soluble | 11.6% |
| Comparative Solvent 6 | Totally Soluble | Totally Soluble | N/A |
| Comparative Solvent 7 | Totally Soluble | Totally Soluble | ~10% |
| Comparative Solvent 8 | Totally Soluble | Totally Soluble | N/A |
| Comparative Solvent 9 | Totally Soluble | Totally Soluble | N/A |
| Comparative Solvent 10 | Totally Soluble | Totally Soluble | N/A |
| Comparative Solvent 11 | Totally Soluble | Totally Soluble | ~20% |
| Comparative Solvent 12 | Totally Soluble | Totally Soluble | 6.89% |

| Approximate Percent (%) Solubility Determination of Active Components in Solvents | Example 1, Comparative Examples A1-L1 (Metolachlor At 54° C.) | Example 2, Comparative Examples A2-L2 (Malathion At 54° C.) | Example 3, Comparative Examples A3-L3 (Propanil At 54° C.) |
|---|---|---|---|
| Solvent 1 | Totally Soluble | Totally Soluble | 29.3% |
| Comparative Solvent 1 | Totally Soluble | Totally Soluble | 55.9 |
| Comparative Solvent 2 | Totally Soluble | Totally Soluble | 48.1% |
| Comparative Solvent 3 | Totally Soluble | Totally Soluble | 29.7% |
| Comparative Solvent 4 | Totally Soluble | Totally Soluble | 24.4% |
| Comparative Solvent 5 | Totally Soluble | Totally Soluble | 59.6% |
| Comparative Solvent 6 | Totally Soluble | Totally Soluble | N/A |
| Comparative Solvent 7 | Totally Soluble | Totally Soluble | ~40% |
| Comparative Solvent 8 | Totally Soluble | Totally Soluble | N/A |
| Comparative Solvent 9 | Totally Soluble | Totally Soluble | N/A |
| Comparative Solvent 10 | Totally Soluble | Totally Soluble | N/A |
| Comparative Solvent 11 | Totally Soluble | Totally Soluble | ~35% |
| Comparative Solvent 12 | Totally Soluble | Totally Soluble | 32.0% |

The terminology "totally soluble" corresponds to an evaluation that no particles of the particular active component are visually detectable in the Solvents.

The numerical percentages in Table 2 indicate the weight percent of the Propanil that was determined to be soluble in the Solvents at the various temperatures.

The results set forth in Table 2 above demonstrate that the Solvent 1, i.e., 1,2-cyclohexanedicarboxylic acid diisononyl ester (Hexamoll® Dinch), of this invention effectively dissolves the three common active components as well or better than each of the Comparative Solvents 1-13. Coupled with the decreased VOC content data set forth in Table 1, the data of Table 2 further supports the special results achieved by the instant invention.

Determination of Active Component Solubility in Various Solvents at 25° C. and 40° C.:

Examples 4 and 5 and Comparative Examples A4-L4 are formed as described above and include 5 grams of Propanil added to 10 grams of Solvent. Each of Examples 4 and 5 and Comparative Examples A4-L4 is prepared in duplicate, as described above. One sample of each of the Examples 4 and 5 and Comparative Examples A4-L4 is stored at 25° C. while a second sample of each is stored at 40° C. for approximately two weeks. After this time, the samples of Solvent 1 and Comparative Solvents 1-5, & 12 are evaluated to determine the solubility of Propanil, as described above, using HPLC. The solubility of Propanil in the samples of the other solvents at 25° C. is determined visually. The results of these evaluations are set forth in Table 3 below.

Example 6 and Comparative Examples A6-L6 are formed by adding one gram of Endosulfan, also a non-limiting example of a suitable active component, to 9 grams of various solvents to form solutions which are mixed at 25° C. until equilibrium is reached. At equilibrium, each solution is visually evaluated to determine whether any undissolved Endosulfan remains. If all of the Endosulfan is dissolved, additional Endosulfan is added in 0.25 gram increments until, at equilibrium, no additional Endosulfan dissolves. The results of these evaluations are also set forth in Table 3 below.

TABLE 3

| Approximate Percent (%) Solubility Determination of Active Components in Solvents | Example 4, Comparative Examples A4-L4 (Propanil At 25° C.) | Example 5, Comparative Examples A4-L4 (Propanil At 40° C.) | Example 6, Comparative Examples A6-L6 (Endosulfan At 25° C.) |
|---|---|---|---|
| Solvent 1 | 27.9% | 37.7% | 32% |
| Comparative Solvent 1 | 23.5% | 39.4% | 28% |
| Comparative Solvent 2 | 7.1% | 18.2% | 55% |
| Comparative Solvent 3 | 20.5% | 24.0% | N/A |
| Comparative Solvent 4 | 19.6% | 19.2% | N/A |
| Comparative Solvent 5 | 25.0% | 31.0% | N/A |
| Comparative Solvent 6 | 28.5% | N/A | 40% |
| Comparative Solvent 7 | 22.0% | ~28% | N/A |
| Comparative Solvent 8 | 60% | N/A | 53% |
| Comparative Solvent 9 | 31.1% | N/A | N/A |
| Comparative Solvent 10 | 32.8% | N/A | N/A |
| Comparative Solvent 11 | 28.5% | ~30% | 42% |
| Comparative Solvent 12 | 13.5% | 22.2% | 29% |

The numerical percentages in Table 3 indicate the weight percent of the Propanil or Endosulfan that was determined to be soluble in the Solvents at the various temperatures.

The results set forth in Table 3 above further demonstrate that the Solvent 1, i.e., 1,2-cyclohexanedicarboxylic acid diisononyl ester (Hexamoll® Dinch), of this invention effectively dissolves Propanil in amounts in excess of most other solvents and that Solvent 1 also effectively dissolved Endosulfan. Coupled with the data set forth above, the data of Table 3 even further supports the special results achieved by the instant invention.

Variations in Amount of Emulsifier Component:

Six series of emulsions are formed and utilize the Solvent 1 of this invention. These emulsions are formed by diluting various emulsifiable concentrates to 5% by volume in hard water (~342 ppm calcium). Emulsions 1-18 include emulsifiable concentrates of this invention. Comparative Emulsions 1-72 do not include emulsifiable concentrates of this invention because, in each Comparative Emulsion, one or more of the anionic, non-ionic, or surfactant including the at least one ethylene oxide block, is missing.

Each of the Emulsions 1-15 and Comparative Emulsions 1-60 includes approximately 60 wt % of Metolachlor, approximately 35 wt % of Hexamoll® Dinch, and approximately 5 wt % of the surfactants.

Each of the Emulsions 16-18 and Comparative Emulsions 61-72 includes approximately 60 wt % of Metolachlor, approximately 33 wt % of Hexamoll® Dinch, and approximately 7 wt % of the surfactants.

After formation, each of the Emulsions is visually evaluated to determine emulsion characteristics. More specifically, bloom, 30 minute stability, 2 hour stability, 24 hour stability, and final stability is evaluated on a numerical scale of 1-5. Relative to bloom, the numerical scale is as follows: 5=excellent; 4=good; 3=fair; 2=poor; and 1=none. As is well known in the art, blooming of emulsions is desirable and refers to spontaneous formation of an emulsion without additional of external forces such as mixing or vortexing. Relative to stability, the numerical scale is as follows: 5=excellent wherein the emulsion is milky in color and has <1 mm of settling and/or phase separation; 4=good wherein the emulsion is milky in color with >1 mm of settling and/or phase separation; 3=fair wherein the emulsion is cloudy with or without settling and/or phase separation; 2=poor wherein the emulsion is watery with some haze and obvious settling and/or phase separation; 1=no emulsion is formed and there is total phase separation. Final stability is assessed after 24 hours by inverting each of the Emulsions to ensure mixing, allowing each of the Emulsions to rest for 30 minutes, and then re-evaluating each of the Emulsions according to the criteria described immediately above.

Formation and Evaluation of Emulsions 1-3 and Comparative Emulsions 1-12:

To form Emulsions 1-3 and Comparative Emulsions 1-12, varying amounts of an anionic surfactant, a non-ionic surfactant, and a surfactant including the at least one ethylene oxide block are utilized, as set forth in Table 4 below. For these emulsions, the anionic surfactant is Witconate® P-1220EH which is commercially available from AkzoNobel. The non-ionic surfactant is Emulpon® CO-550 which is also commercially available from AkzoNobel. The surfactant including the at least one ethylene oxide block is Tergitol® XD which is commercially available from The Dow Chemical Company.

TABLE 4

| Emulsion | Grams of Anionic Surfactant | Grams of Non-Ionic Surfactant | Grams Of Surfactant Including The At Least One Ethylene Oxide Block | Total Grams of Surfactants |
|---|---|---|---|---|
| Emulsion 1 | 0.5 | 0.5 | 1 | 2 |
| Emulsion 2 | 0.5 | 1 | 0.5 | 2 |
| Emulsion 3 | 1 | 0.5 | 0.5 | 2 |
| Comparative Emulsion 1 | 0 | 0 | 2 | 2 |
| Comparative Emulsion 2 | 0 | 0.5 | 1.5 | 2 |
| Comparative Emulsion 3 | 0.5 | 0 | 1.5 | 2 |
| Comparative Emulsion 4 | 1 | 0 | 1 | 2 |
| Comparative Emulsion 5 | 0 | 1 | 1 | 2 |
| Comparative Emulsion 6 | 1.5 | 0 | 0.5 | 2 |
| Comparative Emulsion 7 | 0 | 1.5 | 0.5 | 2 |
| Comparative Emulsion 8 | 2 | 0 | 0 | 2 |
| Comparative Emulsion 9 | 1 | 1 | 0 | 2 |
| Comparative Emulsion 10 | 1.5 | 0.5 | 0 | 2 |
| Comparative Emulsion 11 | 0.5 | 1.5 | 0 | 2 |
| Comparative Emulsion 12 | 0 | 2 | 0 | 2 |

| Emulsion | Bloom | 30 min Stability | 2 hr Stability | 24 hr Stability | Final Stability |
|---|---|---|---|---|---|
| Emulsion 1 | 2 | 3 | 3 | 3 | 3 |
| Emulsion 2 | 2 | 4 | 4 | 4 | 4 |
| Emulsion 3 | 3 | 5 | 5 | 5 | 5 |
| Comparative Emulsion 1 | 1 | 1 | 1 | 1 | 1 |
| Comparative Emulsion 2 | 1 | 1 | 1 | 1 | 1 |
| Comparative Emulsion 3 | 2 | 4 | 4 | 4 | 4 |
| Comparative Emulsion 4 | 3 | 5 | 4 | 4 | 4 |
| Comparative Emulsion 5 | 1 | 1 | 1 | 1 | 1 |
| Comparative Emulsion 6 | 4 | 5 | 5 | 2 | 2 |
| Comparative Emulsion 7 | 1 | 1 | 1 | 1 | 1 |
| Comparative Emulsion 8 | 1 | 3 | 3 | 3 | 3 |
| Comparative Emulsion 9 | 3 | 3 | 3 | 3 | 3 |

TABLE 4-continued

| | | | | | |
|---|---|---|---|---|---|
| Comparative Emulsion 10 | 3 | 5 | 5 | 2 | 2 |
| Comparative Emulsion 11 | 3 | 3 | 3 | 3 | 3 |
| Comparative Emulsion 12 | 2 | 2 | 2 | 2 | 2 |

Formation and Evaluation of Emulsions 4-6 and Comparative Emulsions 13-24:

To form Emulsions 4-6 and Comparative Emulsions 13-24, varying amounts of an anionic surfactant, a non-ionic surfactant, and a surfactant including the at least one ethylene oxide block are utilized, as set forth in Table 5 below. For these emulsions, the anionic surfactant is Witconate® P-1220EH which is commercially available from AkzoNobel. The non-ionic surfactant is Cremophor® CO 40 which is commercially available from BASF Corporation. The surfactant including the at least one ethylene oxide block is Pluriol® WSB 125 which is also commercially available from BASF Corporation.

TABLE 5

| Emulsion | Grams of Anionic Surfactant | Grams of Non-Ionic Surfactant | Grams Of Surfactant Including The At Least One Ethylene Oxide Block | Total Grams of Surfactants |
|---|---|---|---|---|
| Emulsion 4 | 1.25 | 1.25 | 2.5 | 5 |
| Emulsion 5 | 1.25 | 2.5 | 1.25 | 5 |
| Emulsion 6 | 2.5 | 1.25 | 1.25 | 5 |
| Comparative Emulsion 13 | 0 | 0 | 5 | 5 |
| Comparative Emulsion 14 | 0 | 1.25 | 3.75 | 5 |
| Comparative Emulsion 15 | 1.25 | 0 | 3.75 | 5 |
| Comparative Emulsion 16 | 2.5 | 0 | 2.5 | 5 |
| Comparative Emulsion 17 | 0 | 2.5 | 2.5 | 5 |
| Comparative Emulsion 18 | 3.75 | 0 | 1.25 | 5 |
| Comparative Emulsion 19 | 0 | 3.75 | 1.25 | 5 |
| Comparative Emulsion 20 | 5 | 0 | 0 | 5 |
| Comparative Emulsion 21 | 2.5 | 2.5 | 0 | 5 |
| Comparative Emulsion 22 | 3.75 | 1.25 | 0 | 5 |
| Comparative Emulsion 23 | 1.25 | 3.75 | 0 | 5 |
| Comparative Emulsion 24 | 0 | 5 | 0 | 5 |

| Emulsion | Bloom | 30 min Stability | 2 hr Stability | 24 hr Stability | Final Stability |
|---|---|---|---|---|---|
| Emulsion 4 | 1 | 1 | 1 | 1 | 2 |
| Emulsion 5 | 1 | 1 | 1 | 1 | 3 |
| Emulsion 6 | 4 | 5 | 5 | 5 | 5 |
| Comparative Emulsion 13 | 1 | 1 | 1 | 1 | 1 |
| Comparative Emulsion 14 | 1 | 1 | 1 | 1 | 1 |
| Comparative Emulsion 15 | 1 | 1 | 1 | 1 | 1 |
| Comparative Emulsion 16 | 5 | 5 | 4.5 | 4 | 5 |
| Comparative Emulsion 17 | 2 | 1 | 1 | 1 | 1 |
| Comparative Emulsion 18 | 3 | 5 | 4.5 | 3 | 4 |
| Comparative Emulsion 19 | 1 | 1 | 1 | 1 | 3 |
| Comparative Emulsion 20 | 1 | 3.5 | 3.5 | 3 | 3.5 |
| Comparative Emulsion 21 | 2 | 4 | 4 | 3 | 3.5 |
| Comparative Emulsion 22 | 4 | 4 | 4 | 2 | 3.5 |
| Comparative Emulsion 23 | 2 | 4 | 4 | 4 | 4 |
| Comparative Emulsion 24 | 3 | 4 | 3 | 1 | 3 |

Formation and Evaluation of Emulsions 7-9 and Comparative Emulsions 25-34:

To form Emulsions 7-9 and Comparative Emulsions 25-36, varying amounts of an anionic surfactant, a non-ionic surfactant, and a surfactant including the at least one ethylene oxide block are utilized, as set forth in Table 6 below. For these emulsions, the anionic surfactant is Witconate® P-1220EH which is commercially available from AkzoNobel. The non-ionic surfactant is Emulpon® CO-550 which is also commercially available from AkzoNobel. The surfactant including the at least one ethylene oxide block is Pluriol® WSB 125 which is also commercially available from BASF Corporation.

TABLE 6

| Emulsion | Grams of Anionic Surfactant | Grams of Non-Ionic Surfactant | Grams Of Surfactant Including The At Least One Ethylene Oxide Block | Total Grams of Surfactants |
|---|---|---|---|---|
| Emulsion 7 | 1.2 | 1.2 | 2.5 | 5 |
| Emulsion 8 | 1.2 | 2.5 | 1.2 | 5 |
| Emulsion 9 | 2.5 | 1.2 | 1.2 | 5 |
| Comparative Emulsion 25 | 0 | 0 | 5 | 5 |
| Comparative Emulsion 26 | 0 | 1.25 | 3.75 | 5 |
| Comparative Emulsion 27 | 1.25 | 0 | 3.75 | 5 |
| Comparative Emulsion 28 | 2.5 | 0 | 2.5 | 5 |
| Comparative Emulsion 29 | 0 | 2.5 | 2.5 | 5 |
| Comparative Emulsion 30 | 3.75 | 0 | 1.25 | 5 |
| Comparative Emulsion 31 | 0 | 3.75 | 1.25 | 5 |
| Comparative Emulsion 32 | 5 | 0 | 0 | 5 |
| Comparative Emulsion 33 | 2.5 | 2.5 | 0 | 5 |
| Comparative Emulsion 34 | 3.75 | 1.25 | 0 | 5 |
| Comparative Emulsion 35 | 1.25 | 3.75 | 0 | 5 |
| Comparative Emulsion 36 | 0 | 5 | 0 | 5 |

| Emulsion | Bloom | 30 min Stability | 2 hr Stability | 24 hr Stability | Final Stability |
|---|---|---|---|---|---|
| Emulsion 7 | 3 | 4 | 4 | 4 | 4 |
| Emulsion 8 | 3 | 4 | 4 | 4 | 4 |
| Emulsion 9 | 4 | 4 | 4 | 4 | 4 |
| Comparative Emulsion 25 | N/A | N/A | N/A | N/A | N/A |
| Comparative Emulsion 26 | 1 | 1 | 1 | 1 | 1 |
| Comparative Emulsion 27 | N/A | N/A | N/A | N/A | N/A |

TABLE 6-continued

| | | | | | |
|---|---|---|---|---|---|
| Comparative Emulsion 28 | N/A | N/A | N/A | N/A | N/A |
| Comparative Emulsion 29 | 1 | 1 | 1 | 1 | 1 |
| Comparative Emulsion 30 | N/A | N/A | N/A | N/A | N/A |
| Comparative Emulsion 31 | 2 | 1.5 | 1 | 1 | 2 |
| Comparative Emulsion 32 | N/A | N/A | N/A | N/A | N/A |
| Comparative Emulsion 33 | 3.5 | 4 | 3 | 3 | 4 |
| Comparative Emulsion 34 | 3 | 4 | 4 | 2 | 4 |
| Comparative Emulsion 35 | 2 | 3 | 3 | 3 | 3.5 |
| Comparative Emulsion 36 | 3 | 2 | 2 | 1 | 3 |

Formation and Evaluation of Emulsions 10-12 and Comparative Emulsions 37-48:

To form Emulsions 10-12 and Comparative Emulsions 37-48, varying amounts of an anionic surfactant, a non-ionic surfactant, and a surfactant including the at least one ethylene oxide block are utilized, as set forth in Table 7 below. For these emulsions, the anionic surfactant is Witconate® P-1220EH which is commercially available from AkzoNobel. The non-ionic surfactant is a 50/50 weight blend of Lutensol® AO3 and Lutensol® XL 100, each of which is commercially available from BASF Corporation. The surfactant including the at least one ethylene oxide block is Pluriol® WSB 125 which is also commercially available from BASF Corporation.

TABLE 7

| Emulsion | Grams of Anionic Surfactant | Grams of Non-Ionic Surfactant | Grams Of Surfactant Including The At Least One Ethylene Oxide Block | Total Grams of Surfactants |
|---|---|---|---|---|
| Emulsion 10 | 1.25 | 1.25 | 2.5 | 5 |
| Emulsion 11 | 1.25 | 2.5 | 1.25 | 5 |
| Emulsion 12 | 2.5 | 1.25 | 1.25 | 5 |
| Comparative Emulsion 37 | 0 | 0 | 5 | 5 |
| Comparative Emulsion 38 | 0 | 1.25 | 3.75 | 5 |
| Comparative Emulsion 39 | 1.25 | 0 | 3.75 | 5 |
| Comparative Emulsion 40 | 2.5 | 0 | 2.5 | 5 |
| Comparative Emulsion 41 | 0 | 2.5 | 2.5 | 5 |
| Comparative Emulsion 42 | 3.75 | 0 | 1.25 | 5 |
| Comparative Emulsion 43 | 0 | 3.75 | 1.25 | 5 |
| Comparative Emulsion 44 | 5 | 0 | 0 | 5 |
| Comparative Emulsion 45 | 2.5 | 2.5 | 0 | 5 |
| Comparative Emulsion 46 | 3.75 | 1.25 | 0 | 5 |
| Comparative Emulsion 47 | 1.25 | 3.75 | 0 | 5 |
| Comparative Emulsion 48 | 0 | 5 | 0 | 5 |

| Emulsion | Bloom | 30 min Stability | 2 hr Stability | 24 hr Stability | Final Stability |
|---|---|---|---|---|---|
| Emulsion 10 | 3 | 3 | 3 | 3 | 3 |
| Emulsion 11 | 3 | 3.5 | 3.5 | 3.5 | 4 |
| Emulsion 12 | 4 | 5 | 4 | 4 | 5 |
| Comparative Emulsion 37 | N/A | N/A | N/A | N/A | N/A |
| Comparative Emulsion 38 | 1 | 1 | 1 | 1 | 1 |
| Comparative Emulsion 39 | N/A | N/A | N/A | N/A | N/A |
| Comparative Emulsion 40 | N/A | N/A | N/A | N/A | N/A |
| Comparative Emulsion 41 | 1 | 1 | 1 | 1 | 1.5 |
| Comparative Emulsion 42 | N/A | N/A | N/A | N/A | N/A |
| Comparative Emulsion 43 | 1 | 2 | 1 | 1 | 2 |
| Comparative Emulsion 44 | N/A | N/A | N/A | N/A | N/A |
| Comparative Emulsion 45 | 1 | 4 | 4 | 3 | 4 |
| Comparative Emulsion 46 | 1 | 4 | 4 | 3 | 3.5 |
| Comparative Emulsion 47 | 1 | 2.5 | N/A | 1.5 | 3 |
| Comparative Emulsion 48 | 1 | 2 | 1 | 1 | 1.5 |

Formation and Evaluation of Emulsions 13-15 and Comparative Emulsions 49-60:

To form Emulsions 13-15 and Comparative Emulsions 49-60, varying amounts of an anionic surfactant, a non-ionic surfactant, and a surfactant including the at least one ethylene oxide block are utilized, as set forth in Table 8 below. For these emulsions, the anionic surfactant is Witconate® P-1220EH which is commercially available from AkzoNobel. The non-ionic surfactant is Emulpon® CO-550 which is also commercially available from AkzoNobel. The surfactant including the at least one ethylene oxide block is Tergitol® XD which is commercially available from The Dow Chemical Company.

TABLE 8

| Emulsion | Grams of Anionic Surfactant | Grams of Non-Ionic Surfactant | Grams Of Surfactant Including The At Least One Ethylene Oxide Block | Total Grams of Surfactants |
|---|---|---|---|---|
| Emulsion 13 | 1.25 | 1.25 | 2.5 | 5 |
| Emulsion 14 | 1.25 | 2.5 | 1.25 | 5 |
| Emulsion 15 | 2.5 | 1.25 | 1.25 | 5 |
| Comparative Emulsion 49 | 0 | 0 | 5 | 5 |
| Comparative Emulsion 50 | 0 | 1.25 | 3.75 | 5 |
| Comparative Emulsion 51 | 1.25 | 0 | 3.75 | 5 |
| Comparative Emulsion 52 | 2.5 | 0 | 2.5 | 5 |
| Comparative Emulsion 53 | 0 | 2.5 | 2.5 | 5 |
| Comparative Emulsion 54 | 3.75 | 0 | 1.25 | 5 |
| Comparative Emulsion 55 | 0 | 3.75 | 1.25 | 5 |
| Comparative Emulsion 56 | 5 | 0 | 0 | 5 |
| Comparative Emulsion 57 | 2.5 | 2.5 | 0 | 5 |
| Comparative Emulsion 58 | 3.75 | 1.25 | 0 | 5 |
| Comparative Emulsion 59 | 1.25 | 3.75 | 0 | 5 |
| Comparative Emulsion 60 | 0 | 5 | 0 | 5 |

TABLE 8-continued

| Emulsion | Bloom | 30 min Stability | 2 hr Stability | 24 hr Stability | Final Stability |
|---|---|---|---|---|---|
| Emulsion 13 | 1.5 | 3 | 3 | 3 | 3 |
| Emulsion 14 | 2 | 4 | 4 | 4 | 4 |
| Emulsion 15 | 3 | 4 | 4 | 4 | 4 |
| Comparative Emulsion 49 | 1 | 1 | 1 | 1 | 1 |
| Comparative Emulsion 50 | 1 | 1 | 1 | 1 | 1 |
| Comparative Emulsion 51 | 1 | 3 | 2 | 2 | 3 |
| Comparative Emulsion 52 | 4 | 4 | 4 | 4 | 5 |
| Comparative Emulsion 53 | 1 | 1 | 1 | 1 | 1 |
| Comparative Emulsion 54 | 4 | 4 | 3 | 1.5 | 3 |
| Comparative Emulsion 55 | 1 | 1 | 1 | 1 | 1 |
| Comparative Emulsion 56 | N/A | N/A | N/A | N/A | N/A |
| Comparative Emulsion 57 | N/A | N/A | N/A | N/A | N/A |
| Comparative Emulsion 58 | N/A | N/A | N/A | N/A | N/A |
| Comparative Emulsion 59 | N/A | N/A | N/A | N/A | N/A |
| Comparative Emulsion 60 | N/A | N/A | N/A | N/A | N/A |

Formation and Evaluation of Emulsions 16-18 and Comparative Emulsions 61-72:

To form Emulsions 16-18 and Comparative Emulsions 61-72, varying amounts of an anionic surfactant, a non-ionic surfactant, and a surfactant including the at least one ethylene oxide block are utilized, as set forth in Table 9 below. For these emulsions, the anionic surfactant is Witconate® P-1220EH which is commercially available from AkzoNobel. The non-ionic surfactant is Cremophor® CO 40 which is commercially available from BASF Corporation. The surfactant including the at least one ethylene oxide block is Pluriol® WSB 125 which is also commercially available from BASF Corporation.

TABLE 9

| Emulsion | Grams of Anionic Surfactant | Grams of Non-Ionic Surfactant | Grams Of Surfactant Including The At Least One Ethylene Oxide Block | Total Grams of Surfactants |
|---|---|---|---|---|
| Emulsion 16 | 1.25 | 1.25 | 2.5 | 5 |
| Emulsion 17 | 1.25 | 2.5 | 1.25 | 5 |
| Emulsion 18 | 2.5 | 1.25 | 1.25 | 5 |
| Comparative Emulsion 61 | 0 | 0 | 5 | 5 |
| Comparative Emulsion 62 | 0 | 1.25 | 3.75 | 5 |
| Comparative Emulsion 63 | 1.25 | 0 | 3.75 | 5 |
| Comparative Emulsion 64 | 2.5 | 0 | 2.5 | 5 |
| Comparative Emulsion 65 | 0 | 2.5 | 2.5 | 5 |
| Comparative Emulsion 66 | 3.75 | 0 | 1.25 | 5 |
| Comparative Emulsion 67 | 0 | 3.75 | 1.25 | 5 |
| Comparative Emulsion 68 | 5 | 0 | 0 | 5 |
| Comparative Emulsion 69 | 2.5 | 2.5 | 0 | 5 |
| Comparative Emulsion 70 | 3.75 | 1.25 | 0 | 5 |
| Comparative Emulsion 71 | 1.25 | 3.75 | 0 | 5 |
| Comparative Emulsion 72 | 0 | 5 | 0 | 5 |

| Emulsion | Bloom | 30 min Stability | 2 hr Stability | 24 hr Stability | Final Stability |
|---|---|---|---|---|---|
| Emulsion 16 | 4 | 4 | 4 | 4 | 4 |
| Emulsion 17 | 3.5 | 4 | 4 | 4 | 4 |
| Emulsion 18 | 4.5 | 5 | 5 | 5 | 5 |
| Comparative Emulsion 61 | 1 | 1 | 1 | 1 | 1 |
| Comparative Emulsion 62 | 1 | 1 | 1 | 1 | 1 |
| Comparative Emulsion 63 | 4 | 4 | 4 | 4 | 4 |
| Comparative Emulsion 64 | 4.5 | 5 | 5 | 5 | 5 |
| Comparative Emulsion 65 | 2 | 2 | 1 | 1 | 2 |
| Comparative Emulsion 66 | 4 | 4 | 4 | 3 | 4 |
| Comparative Emulsion 67 | 3 | 2.5 | 1.5 | 1 | 2 |
| Comparative Emulsion 68 | 1 | 3 | 3 | 2.5 | 3 |
| Comparative Emulsion 69 | 4 | 4 | 4 | 4 | 4 |
| Comparative Emulsion 70 | 3 | 4 | 3.5 | 2 | 4 |
| Comparative Emulsion 71 | 3.5 | 4 | 4 | 4 | 4 |
| Comparative Emulsion 72 | 3 | 3.5 | 3.5 | 2 | 3 |

Two additional emulsions that represent various embodiments of this invention (Emulsions 19 and 20) are also formed and evaluated as described above. More specifically, to form Emulsions 19 and 20, the ratio of emulsifiers was not varied. Instead, an optimal ratio from previous evaluations is used (2:1:1 by weight of anionic surfactant, nonionic surfactant, surfactant including at least one ethylene oxide block). More specifically, about 60 wt % of Metolachlor, about 35 wt % of Hexamoll® Dinch, and approximately 5 wt % of the surfactants are utilized.

To form Emulsion 19, the nonionic surfactant is a 1:1 ratio by weight of Pluronic L43 and Pluronic F77, each of which is commercially available from BASF Corporation. The surfactant including the at least one ethylene oxide block is Pluriol® WSB 125 which is also commercially available from BASF Corporation.

To form Emulsion 20, the nonionic surfactant is a 1:1 ratio by weight of Pluronic L43 and Pluronic F87, each of which is commercially available from BASF Corporation. The surfactant including the at least one ethylene oxide block is Pluriol® WSB 125 which is also commercially available from BASF Corporation.

The components used to form Emulsions 19 and 20, and the results of the evaluations of these Emulsions, are set forth in Table 10 below.

TABLE 10

| Emulsion | Grams of Anionic Surfactant | Grams of Non-Ionic Surfactant | Grams Of Surfactant Including The At Least One Ethylene Oxide Block | Total Grams of Surfactants |
|---|---|---|---|---|
| Emulsion 19 | 2.5 | 1.25 | 1.25 | 5 |
| Emulsion 20 | 2.5 | 1.25 | 1.25 | 5 |

TABLE 10-continued

| Emulsion | Bloom | 30 min Stability | 2 hr Stability | 24 hr Stability | Final Stability |
|---|---|---|---|---|---|
| Emulsion 19 | 4 | 5 | 5 | 5 | 5 |
| Emulsion 20 | 4 | 4 | 4 | 4 | 4 |

The data set forth above, and specifically in Tables 4-10, suggests that a preferred, but non-limiting, weight ratio of anionic surfactant:non-ionic surfactant:ethylene oxide block copolymer surfactant is about 2:1:1. Of course, it is to be understood that the instant invention is not limited to such a ratio.

This data also suggests that the instant invention exhibits special results relative to bloom, 30 minute stability, 2 hour stability, 24 hour stability, and final stability and that the Solvent 1, i.e., 1,2-cyclohexanedicarboxylic acid diisononyl ester (Hexamoll® Dinch), of this invention effectively dissolves four common active components as well or better than most of the Comparative Solvents 1-13. Coupled with the decreased VOC content data set forth in Table 1, the data of Tables 2 and following further supports the special results achieved by the instant invention. More specifically, the data set forth in the Examples generally suggests that the instant invention performs as well or better than many of the comparative examples and does so with a lower VOC content, with lower odor, with an improved toxicological profile, and at a minimized cost. In other words, the instant invention maintains the stability and commercial usefulness of the emulsifiable concentrate at a low cost while allowing the active component to effectively mix with, and remain dissolved in, the solvent component.

It is to be understood that any of the numerical values associated with this invention, e.g. ranges, ratios, etc., are not particularly limiting and may vary. For example, any of the aforementioned numerical values may be further defined as any value or range of values, both whole and fractional, within those ranges and values described above and/or may vary from the values and/or range of values described above by ±5%, ±10%, ±15%, ±20%, ±25%, ±30%, etc, so long as the variations remain within the scope of the invention.

It is also to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is further to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The invention has been described in an illustrative manner, and it is to be understood that the terminology which has been used is intended to be in the nature of words of description rather than of limitation. Many modifications and variations of the present invention are possible in light of the above teachings, and the invention may be practiced otherwise than as specifically described.

What is claimed is:

1. An emulsifiable concentrate comprising:
   A. a solvent component comprising 1,2-cyclohexanedicarboxylic acid diisononyl ester;
   B. an active component present in an amount of from 20 to 90 parts by weight per 100 parts by weight of said emulsifiable concentrate and dissolved in said solvent component; and
   C. an emulsifier component present in an amount of from 5 to 15 parts by weight per 100 parts by weight of said emulsifiable concentrate and comprising;
      (1) an anionic surfactant,
      (2) a non-ionic surfactant, and
      (3) a surfactant different from said (1) anionic surfactant and said (2) non-ionic surfactant and comprising at least one ethylene oxide block, wherein said (1) anionic surfactant, said (2) non-ionic surfactant, and said (3) surfactant comprising at least one ethylene oxide block are present in said emulsifier component in a weight ratio of 2:1:1.

2. An emulsifiable concentrate as set forth in claim 1 wherein said anionic surfactant is present in an amount of from 40 to 60 parts by weight per 100 parts by weight of said emulsifier component.

3. An emulsifiable concentrate as set forth in claim 1 wherein said non-ionic surfactant is present in an amount of from 20 to 30 parts by weight per 100 parts by weight of said emulsifier component.

4. An emulsifiable concentrate as set forth in claim 1 wherein said surfactant comprising at least one ethylene oxide block is present in an amount of from 20 to 30 parts by weight per 100 parts by weight of said emulsifier component.

5. An emulsifiable concentrate as set forth in claim 1 wherein said emulsifiable concentrate comprises less than 1 part by weight of water per 100 parts by weight of said emulsifiable concentrate.

6. An emulsifiable concentrate as set forth in claim 1 wherein said active component is present in an amount of from greater than 60 to 90 parts by weight per 100 parts by weight of said concentrate.

7. An emulsifiable concentrate as set forth in claim 6 wherein said anionic surfactant is present in an amount of from 40 to 60 parts by weight per 100 parts by weight of said emulsifier component.

8. An emulsifiable concentrate as set forth in claim 7 wherein said non-ionic surfactant is present in an amount of from 20 to 30 parts by weight per 100 parts by weight of said emulsifier component.

9. An emulsifiable concentrate as set forth in claim 8 wherein said surfactant comprising at least one ethylene oxide block is present in an amount of from 20 to 30 parts by weight per 100 parts by weight of said emulsifier component.

10. An emulsifiable concentrate as set forth in claim 9 wherein said emulsifiable concentrate comprises less than 1 part by weight of water per 100 parts by weight of said emulsifiable concentrate.

11. An emulsifiable concentrate as set forth in claim 1 wherein said active component is present in an amount of from 20 to 60 parts by weight per 100 parts by weight of said emulsifiable concentrate.

12. An emulsifiable concentrate as set forth in claim 11 wherein said anionic surfactant is present in an amount of from 40 to 60 parts by weight per 100 parts by weight of said emulsifier component.

13. An emulsifiable concentrate as set forth in claim 12 wherein said nonionic surfactant is present in an amount of from 20 to 30 parts by weight per 100 parts by weight of said emulsifier component.

14. An emulsifiable concentrate as set forth in claim 13 wherein said surfactant comprising at least one ethylene oxide block is present in an amount of from 20 to 30 parts by weight per 100 parts by weight of said emulsifier component.

15. An emulsifiable concentrate as set forth in claim 14 wherein said emulsifiable concentrate comprises less than 1 part by weight of water per 100 parts by weight of said emulsifiable concentrate.

16. An emulsifiable concentrate as set forth in claim 1 wherein said active component is present in an amount of about 60 parts by weight per 100 parts by weight of said emulsifiable concentrate.

17. An emulsifiable concentrate as set forth in claim 16 wherein said emulsifier component is present in an amount of from about 5 to 7 parts by weight per 100 parts by weight of said emulsifiable concentrate.

18. An emulsifiable concentrate as set forth in claim 16 wherein said solvent component consists essentially of 1,2-cyclohexanedicarboxylic acid diisononyl ester and is present in an amount of from about 33 to 35 parts by weight per 100 parts by weight of said emulsifiable concentrate.

19. An emulsifiable concentrate as set forth in claim 16 wherein said emulsifiable concentrate comprises less than 1 part by weight of water per 100 parts by weight of said emulsifiable concentrate.

20. An emulsifiable concentrate consisting essentially of:
A. an active component present in an amount of from 20 to 90 parts by weight per 100 parts by weight of said emulsifiable concentrate;
B. 1,2-cyclohexanedicarboxylic acid diisononyl ester; and
C. an emulsifier component present in an amount of from 5 to 15 parts by weight per 100 parts by weight of said emulsifiable concentrate and comprising;
(1) an anionic surfactant,
(2) a non-ionic surfactant, and
(3) a surfactant different from said (1) anionic surfactant and said (2) non-ionic surfactant and comprising at least one ethylene oxide block,
wherein said active component is dissolved in said solvent component, and
wherein said emulsifiable concentrate comprises less than 1 part by weight of water per 100 parts by weight of said emulsifiable concentrate; and wherein said (1) anionic surfactant, said (2) non-ionic surfactant, and said (3) surfactant comprising at least one ethylene oxide block are present in said emulsifier component in a weight ratio of 2:1:1.

21. An agricultural emulsion comprising:
A. an emulsifiable concentrate present in an amount of from 10 to 90 parts by weight per 100 parts by weight of said agricultural emulsion and including;
(i) an active component present in an amount of from 20 to 90 parts by weight per 100 parts by weight of said emulsifiable concentrate,
(ii) a solvent component comprising 1,2-cyclohexanedicarboxylic acid diisononyl ester, and
(iii) an emulsifier component present in an amount of from 5 to 15 parts by weight per 100 parts by weight of said emulsifiable concentrate and comprising,
(1) an anionic surfactant,
(2) a non-ionic surfactant, and
(3) a surfactant different from said (1) anionic surfactant and said (2) nonionic surfactant and comprising at least one ethylene oxide block, wherein said active component is dissolved in said solvent component; and
B. water present in an amount of from 10 to 90 parts by weight per 100 parts by weight of said agricultural emulsion, and wherein said (1) anionic surfactant, said (2) non-ionic surfactant, and said (3) surfactant comprising at least one ethylene oxide block are present in said emulsifier component in a weight ratio of 2:1:1.

22. An agricultural emulsion as set forth in claim 21 consisting essentially of said emulsifiable concentrate and said water.

23. An agricultural emulsion as set forth in claim 21 consisting of said emulsifiable concentrate and said water.

24. An emulsifiable concentrate as set forth in claim 1 wherein said anionic surfactant is present in an amount of from 40 to 60 parts by weight per 100 parts by weight of said emulsifier component, said non-ionic surfactant is present in an amount of from 20 to 30 parts by weight per 100 parts by weight of said emulsifier component, said surfactant comprising at least one ethylene oxide block is present in an amount of from 20 to 30 parts by weight per 100 parts by weight of said emulsifier component, and said emulsifiable concentrate comprises less than 1 part by weight of water per 100 parts by weight of said emulsifiable concentrate.

25. An emulsifiable concentrate comprising:
A. a solvent component comprising 1,2-cyclohexanedicarboxylic acid diisononyl ester;
B. an active component present in an amount of from 20 to 90 parts by weight per 100 parts by weight of said emulsifiable concentrate and dissolved in said solvent component; and
C. an emulsifier component present in an amount of from 5 to 15 parts by weight per 100 parts by weight of said emulsifiable concentrate and comprising;
(1) an anionic surfactant,
(2) a non-ionic surfactant, and
(3) a surfactant different from said (1) anionic surfactant and said (2) non-ionic surfactant and comprising at least one ethylene oxide block, wherein said anionic surfactant is present in an amount of from 40 to 60 parts by weight per 100 parts by weight of said emulsifier component, said non-ionic surfactant is present in an amount of from 20 to 80 parts by weight per 100 parts by weight of said emulsifier component, said surfactant comprising at least one ethylene oxide block is present in an amount of from 20 to 80 parts by weight per 100 parts by weight of said emulsifier component.

* * * * *